US011897672B2

(12) United States Patent
Upchurch et al.

(10) Patent No.: US 11,897,672 B2
(45) Date of Patent: Feb. 13, 2024

(54) SLEEVE CONTAINERS FOR PACKAGING MEDICINAL PRODUCTS

(71) Applicant: AbbVie Inc., North Chicago, IL (US)

(72) Inventors: Guy C. Upchurch, Chicago, IL (US); James J. Hughes, Libertyville, IL (US); Jovo Dragicevic, Gurnee, IL (US)

(73) Assignee: ABBVIE INC., North Chicago, IL (US)

( * ) Notice: Subject to any disclaimer, the term of this patent is extended or adjusted under 35 U.S.C. 154(b) by 292 days.

(21) Appl. No.: 17/093,168

(22) Filed: Nov. 9, 2020

(65) Prior Publication Data

US 2021/0139190 A1    May 13, 2021

Related U.S. Application Data

(60) Provisional application No. 62/932,087, filed on Nov. 7, 2019.

(51) Int. Cl.
*B65D 5/48* (2006.01)
*B65D 5/02* (2006.01)
*B65D 5/04* (2006.01)
*B65D 5/50* (2006.01)
*A61M 5/00* (2006.01)

(52) U.S. Cl.
CPC ........... *B65D 5/5002* (2013.01); *A61M 5/002* (2013.01); *B65D 5/029* (2013.01); *B65D 5/0254* (2013.01); *B65D 5/04* (2013.01); *B65D 5/48014* (2013.01)

(58) Field of Classification Search
CPC .... B65D 5/029; B65D 5/46088–46144; B65D 5/04; B65D 5/5002; B65D 5/5004; B65D 5/4212; B65D 5/425; A61M 5/002

USPC ....... 229/117.14, 120.01; 206/364–366, 418, 206/45.29, 766

See application file for complete search history.

(56) References Cited

U.S. PATENT DOCUMENTS

| | | | | |
|---|---|---|---|---|
| 1,683,100 A | * | 9/1928 | Rozowsky | ........... B65D 81/368 |
| | | | | 229/152 |
| 2,225,492 A | * | 12/1940 | Warrick | ............. B65D 5/46088 |
| | | | | 229/117.14 |
| 3,331,550 A | * | 7/1967 | Krzyzanowski | ......... B65D 5/04 |
| | | | | 229/161 |

(Continued)

FOREIGN PATENT DOCUMENTS

| | | | |
|---|---|---|---|
| CA | 2097735 A1 | 12/1994 | |
| CH | 711693 A1 * | 4/2017 | ............... B65D 5/38 |

(Continued)

*Primary Examiner* — Nathan J Newhouse
*Assistant Examiner* — Phillip D Schmidt
(74) *Attorney, Agent, or Firm* — Armstrong Teasdale LLP

(57) ABSTRACT

A blank of sheet material for forming a sleeve container, the blank of sheet material including two side panels each including a bottom edge and a top edge, and two elongated side panels arranged alternatingly with the side panels. A plurality of fold lines are defined between the side panels and the elongated side panels, and the elongated side panels include a side panel portion and a guide flap extending beyond the top edge of the side panels. The side panels and the side panel portions are configured to define an interior cavity of the sleeve container, and the guide flaps are configured to define an insertion guide channel that is in communication with the interior cavity.

17 Claims, 17 Drawing Sheets

(56) References Cited

U.S. PATENT DOCUMENTS

| | | | | |
|---|---|---|---|---|
| 3,337,033 | A | * | 8/1967 | Cote .................... B65D 5/5009 229/128 |
| 3,372,798 | A | * | 3/1968 | John .................... A61M 5/002 206/229 |
| 3,921,895 | A | | 11/1975 | Ziche |
| 4,651,919 | A | * | 3/1987 | Wischusen, III .. B65D 5/46112 229/117.14 |
| 4,717,022 | A | * | 1/1988 | Combs ................. B65D 5/5009 229/109 |
| D302,948 | S | | 8/1989 | Blum et al. |
| 5,566,828 | A | | 10/1996 | Claes et al. |
| 6,068,181 | A | * | 5/2000 | Cai ..................... B65D 33/004 229/906 |
| 6,357,652 | B1 | * | 3/2002 | Evans ................... B65D 55/06 493/383 |
| 6,910,582 | B2 | * | 6/2005 | Lantz ................. B65D 81/3862 206/593 |
| D553,246 | S | | 10/2007 | Banryu |
| D554,261 | S | | 10/2007 | Meoli |
| D585,139 | S | | 1/2009 | Andrews |
| D602,162 | S | | 10/2009 | Albrecht |
| 7,806,262 | B2 | * | 10/2010 | Sakai ................... B65D 5/504 206/370 |
| 7,850,646 | B2 | | 12/2010 | Segal et al. |
| D632,560 | S | | 2/2011 | Caldwell et al. |
| D632,795 | S | | 2/2011 | Matrunola |
| D639,679 | S | | 6/2011 | Kissner et al. |
| D642,934 | S | | 8/2011 | Ly |
| D654,810 | S | | 2/2012 | Mansouri |
| D701,605 | S | | 3/2014 | Ohmukai |
| 8,727,117 | B2 | | 5/2014 | Maasarani |
| 8,925,723 | B2 | * | 1/2015 | Folchini ............... B65D 5/5007 206/370 |
| D742,759 | S | | 11/2015 | Ryan |
| 9,216,124 | B2 | | 12/2015 | Spendley |
| D774,195 | S | | 12/2016 | Ramos |
| D787,312 | S | | 5/2017 | Peers et al. |
| D826,706 | S | | 8/2018 | Moskovich et al. |
| D911,528 | S | | 2/2021 | Sun |
| D921,492 | S | | 6/2021 | Uyeda |
| D932,921 | S | | 10/2021 | Rosenbrien |
| D951,778 | S | | 5/2022 | Upchurch |
| D954,563 | S | | 6/2022 | Upchurch |
| 2008/0135606 | A1 | * | 6/2008 | Weston ................. A61M 5/002 229/124 |
| 2009/0065560 | A1 | * | 3/2009 | Johnson ............... B65D 5/4216 206/581 |
| 2020/0039681 | A1 | | 2/2020 | Monti |
| 2020/0255181 | A1 | | 8/2020 | Sherman et al. |

FOREIGN PATENT DOCUMENTS

| | | | |
|---|---|---|---|
| CN | 2883187 Y | | 3/2007 |
| CN | 101983161 A | | 3/2011 |
| CN | 208785272 U | | 4/2019 |
| EP | 0616950 A1 | | 9/1994 |
| EP | 1733973 A1 | | 12/2006 |
| GB | 980051 A | * | 1/1965 |
| JP | 2001002168 A | | 1/2001 |
| JP | 2018002180 A | | 1/2018 |
| TW | I466804 B | | 1/2015 |
| WO | WO-2005051801 A1 | * | 6/2005 ............... B65D 5/38 |

\* cited by examiner

SLEEVE CONTAINERS FOR PACKAGING MEDICINAL PRODUCTS

CROSS-REFERENCE TO RELATED APPLICATIONS

This application claims priority to U.S. Provisional Application No. 62/932,087, filed on Nov. 7, 2019, which is hereby incorporated by reference in its entirety.

BACKGROUND

The field of the present disclosure relates generally to medication packaging and, more specifically, to sleeve containers for packaging and transporting combination products (i.e., medicinal products) such as pre-filled syringes, vials, and/or auto-injectors.

To receive prescription medicines, patients need to acquire a prescription prepared by a person authorized to prescribe medicine. A prescription medicine is then dispensed by a pharmacist, and the prescription medicine typically comes with an information leaflet providing information about the medicine, its side effects, if any, instructions for use of the medicine, and any relevant cautions and warnings.

At least some known prescription medicines, such as injectable medicines, are provided to a consumer in the form of combination products such as pre-filled syringes, vials, and/or auto-injectors. The combination products are typically filled with the injectable medicine and then packaged for storage and delivery to the patient. Traditional packaging of the combination products may include inner packaging such as blister packs, trays, or paperboard holding slots designed to hold one or more combination products. The inner packaging may then be packaged within an outer paperboard carton, for example, to facilitate storage and transport of multiple combination products to the consumer. However, the traditional packaging can become bulky and large in size, which results in higher material usage and cost to assembly, generation of more post-consumer waste, difficulty in handling and opening by the patient, and potential inconvenience to patients having limited storage space for medicinal products.

In addition, blister packs for example, which are formed from a blister tray and a sealing lid or film, require the use of special thermoforming machines and multi-material construction to be manufactured. Different equipment is used to form, fill, and seal the blister packs, thereby reducing the flexibility of a medicine provider to manually assemble a combination product for small volume runs. Also, it is generally difficult to incorporate special product protection features, such as to protect the medicine from exposure to light, into blister packs. Some consumers may also find traditional blister packs to be difficult to open, such as elderly or dexterity-challenged patients.

BRIEF DESCRIPTION

In one aspect, a blank of sheet material for forming a sleeve container is provided. The blank of sheet material includes two side panels each including a bottom edge and a top edge, and two elongated side panels arranged alternatingly with the side panels. A plurality of fold lines are defined between the side panels and the elongated side panels, and the elongated side panels include a side panel portion and a guide flap extending beyond the top edge of the side panels. The side panels and the side panel portions are configured to define an interior cavity of the sleeve container, and the guide flaps are configured to define an insertion guide channel that is in communication with the interior cavity.

In another aspect, a sleeve container is provided. The sleeve container includes two side walls each including a bottom edge and a top edge, and two elongated side walls arranged alternatingly with the side walls. A plurality of fold lines are defined between the side walls and the elongated side walls, and the elongated side walls include a side wall portion and a guide flap extending beyond the top edge of the side walls. The side walls and the side wall portions define a sleeve portion of the sleeve container. The sleeve portion includes an interior cavity, and the guide flaps are configured to define an insertion guide channel that is in communication with the interior cavity.

In yet another aspect, a container assembly formed from a plurality of blanks of sheet material is provided. The container assembly includes a medication delivery system and a carton. The medication delivery system includes a sleeve container configured to receive an injection medical device. The sleeve container includes two side walls each including a bottom edge and a top edge, and two elongated side walls arranged alternatingly with the side walls. A plurality of fold lines are defined between the side walls and the elongated side walls, and the elongated side walls include a side wall portion and a guide flap extending beyond the top edge of the side walls. The side walls and the side wall portions define a sleeve portion of the sleeve container. The sleeve portion includes an interior cavity, and the guide flaps are configured to define an insertion guide channel that is in communication with the interior cavity. The carton includes a container portion including an interior, and a holder insert positioned within the interior. The holder insert includes a first slot configured to receive the sleeve portion of the sleeve container, and a second slot configured to receive a portion of the injection medical device.

DETAILED DESCRIPTION

Figure 1:
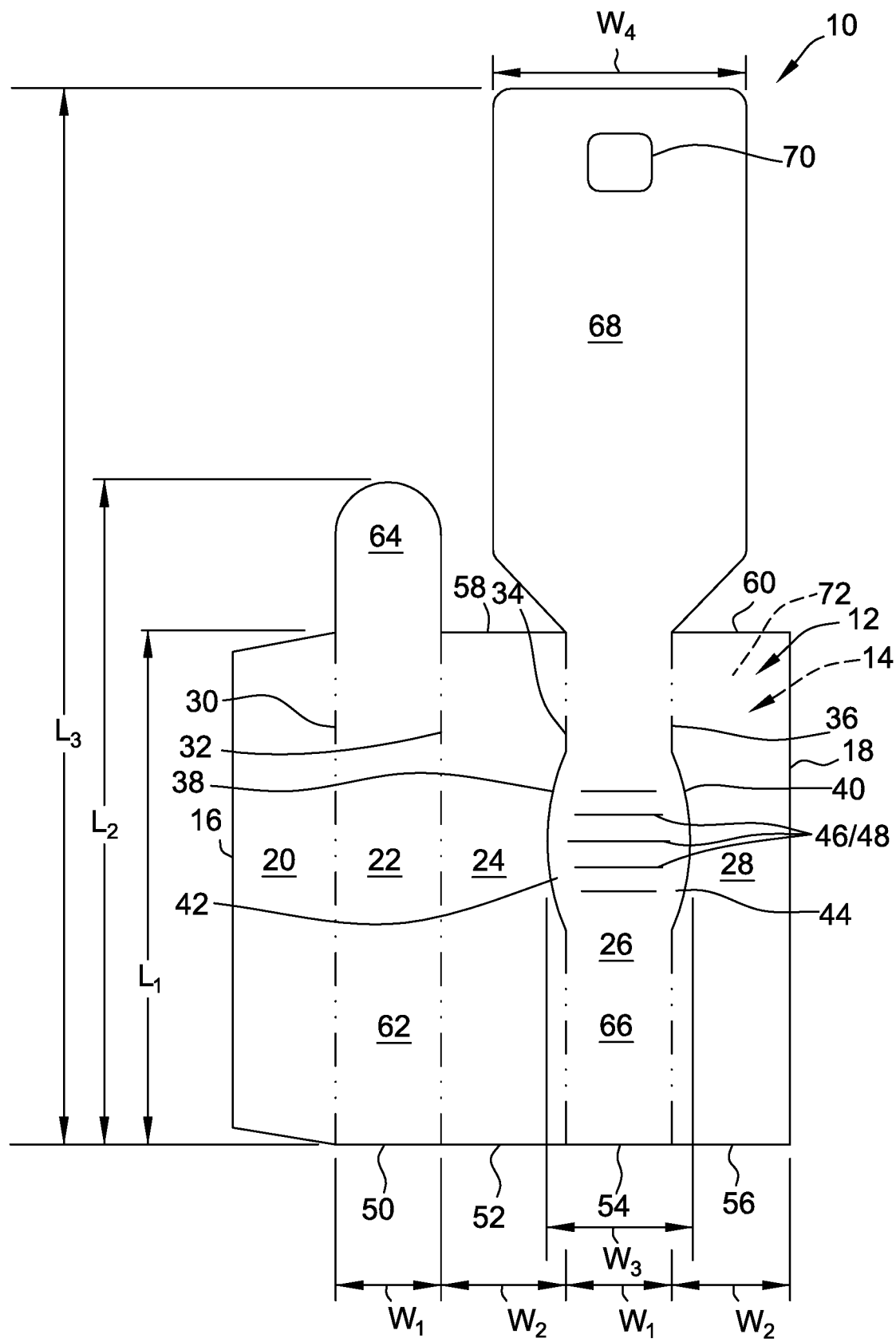
FIG. 1 illustrates a blank of sheet material for forming an example sleeve container.

The following detailed description illustrates the disclosure by way of example and not by way of limitation. The description enables one skilled in the art to make and use the disclosure, describes several embodiments, adaptations, variations, alternatives, and use of the disclosure, including what is presently believed to be the best mode of carrying out the disclosure.

Embodiments of the present disclosure relate to sleeve containers for packaging and transporting combination products (i.e., medicinal products) such as pre-filled syringes, vials, and/or auto-injectors. In some embodiments, the combination product has a barrel and a plunger. The sleeve containers described herein include a sleeve portion having an interior cavity, and guide flaps that define an insertion guide channel that is in communication with the interior cavity. The combination product is insertable within the sleeve container, either manually or with automated production equipment, to facilitate protecting the combination product during storage and transportation. For example, the combination product may be guided barrel-first through the insertion guide channel and then positioned within the sleeve portion of the sleeve container. The size of the sleeve portion is selected to engage the barrel of the combination product with an interference fit to facilitate securing the combination product within the sleeve container. The holding force provided by the interference fit enables the combination product to be removed from the sleeve container with nominal effort when it is time to administer the injectable medicine to the consumer, for example. Accordingly, even patients with limited dexterity may gain access to the combination product contained within the sleeve container without aid or assistance from a caregiver or healthcare provider.

When assembled, the sleeve container and combination product may be positioned within an outer carton that includes a container portion and a holder insert positioned within the container portion. The sleeve container and the holder insert are designed to engage each other in a manner that restricts movement of the sleeve container, and thus the combination product, relative to the container portion. Engagement between the sleeve container and the holder insert also facilitates diverting shock and vibrational forces acting on the outer carton to the sleeve container, rather than to physical components of the combination product. Accordingly, the outer carton provides containment and protection for the combination product during shipping and handling, for example, in a compact and space-saving manner.

The sleeve container facilitates providing protection to the combination product not only from physical damage, but also from other outside influences. For example, in some embodiments, the injectable medicine contained within the barrel may be degraded by exposure to light. For example, the injectable medicine may be a biological medicine, such as anti IL-23 antibody risankizumab (SKYRIZI). When inserted within the sleeve container, the barrel of the combination product is enclosed by side walls of the sleeve portion. The side walls provide physical protection to the barrel, and also facilitate shielding the injectable medicine contained within the barrel from exposure to light. The side walls may also be lined with a layer of protective material, such as metallic foil and the like. The protective material aids in shielding the injectable medicine from exposure to light, and also provides contact surface free of surface contaminants, such as particulates, inks, coatings, and adhesives, in which to engage the combination product.

The design of the sleeve container also provides functional advantages over other known containment and delivery systems. For example, the sleeve portion of the sleeve container may be partitioned to include more than one interior cavity, each for receiving a distinct combination product therein. With at least some known injectable medicines, multiple injections of the same drug are administered one after the other to provide a full fixed dose volume to the patient. In other embodiments multiple combination products may comprise the same or different drugs, and/or the same or different form (e.g., concentration, volume, formulation) of a drug. In the multi-compartment embodiment of the sleeve container, multiple combination products may be grouped as a set, which encourages proper administration of the injectable medicine by the consumer. In addition, the sleeve container may be formed from a folded blank of sheet material that, when assembled, creates a background in which printed information can be provided. Printed information can include, but is not limited to, patient information, important messaging such as usage instructions, product information, and barcodes. As such, the printed information is conveniently located relative, and in close proximity, to the combination product even when removed from the outer carton, and avoids packaging of an additional separate leaflet.

As noted above, the sleeve containers are formed from folded blanks of sheet material, such as a paperboard material. The containers, however, may be fabricated using any suitable material, and therefore are not limited to a specific type of material. In alternative embodiments, the containers are fabricated using cardboard, plastic, and/or any suitable material known to those skilled in the art and guided by the teachings herein provided.

As used herein, the term "user" means a person or person(s) who is using contents from the system described herein (e.g. a patient for whom the drug/medicine is prescribed), a healthcare provider, and/or a patient assistant providing the contents from the system to the person(s) receiving the contents from the system.

Referring now to the drawings, FIG. 1 illustrates a first blank 10 of sheet material for forming a sleeve container in accordance with one embodiment of the disclosure. In the example embodiment, first blank 10 has a first or exterior surface 12, and an opposing second or interior surface 14. Further, first blank 10 defines a leading edge 16 and an opposing trailing edge 18. Moreover, first blank 10 includes, from leading edge 16 to trailing edge 18, a joining tab 20, a first elongated side panel 22, a first side panel 24, a second elongated side panel 26, and a second side panel 28 coupled together along preformed, generally parallel fold lines 30, 32, 34, and 36, respectively. Side panels 22 and 26 have a first width $W_1$, and side panels 24 and 28 have a second width $W_2$ that is greater than first width $W_1$. However, it should be understood that the plurality of side panels can each have any suitable size, shape, and/or configuration that enables blank 10 and/or the sleeve container to function as described herein. Additionally, although joining tab 20, first elongated side panel 22, first side panel 24, second elongated side panel 26, and second side panel 28 are specifically referred to herein, it should be noted that joining tab 20, first elongated side panel 22, first side panel 24, second elongated side panel 26, and second side panel 28 can collectively be referred to as side panels or side walls.

First elongated side panel 22 extends from joining tab 20 along fold line 30, first side panel 24 extends from first elongated side panel 24 along fold line 32, second elongated side panel 26 extends from first side panel 24 along fold line 34, and second side panel 28 extends from second elongated side panel 26 along fold line 36. In addition, a first cut line 38 is defined along a portion of fold line 34, and a second cut line 40 is defined along a portion of fold line 36. First cut line 38 defines a first gripping flap 42 on second elongated side panel 26, and second cut line 40 defines a second gripping flap 44 on second elongated side panel 26. Cut lines 38 and 40 have an arcuate shape and are convex relative to a centerline of second elongated side panel 26. Accordingly, the portion of second elongated side panel 26 defined between cut lines 38 and 40 has a third width $W_3$ greater than second width $W_2$ of side panel 26 itself. Alternatively, gripping flaps 42 and 44 may have any shape that enables the sleeve container to function as described herein. Second elongated side panel 26 also includes debossing lines 46 on first side 12 thereof. Debossing lines 46 facilitate creating raised surface features 48 on second side 14 of second elongated side panel 26. As will be described in more detail below, raised surface features 48 facilitate engagement between the sleeve container and a product positioned therein.

Fold lines 30, 32, 34, and 36 as well as other fold lines and/or hinge lines described herein, may include any suitable line of weakness and/or line of separation known to those skilled in the art and guided by the teachings herein provided. As shown in the drawings, solid-dot or dashed lines indicate lines of weakness, solid lines indicate cut lines, and line-square lines indicate debossing lines.

Side panels 22, 24, 26, and 28 each include bottom edges 50, 52, 54, and 56, respectively, and which are all aligned with each other. Side panels 24 and 28 also include top edges 58 and 60, respectively, which are aligned with each other. Elongated side panel 22 includes a side wall portion 62 and a guide flap 64, and elongated side panel 26 includes a side wall portion 66 and a guide flap 68. Guide flaps 64 and 68 extend beyond top edges 58 and 60 of side panels 24 and 28. In other words, side panels 24 and 28, and side wall portions 62 and 66 have a first length $L_1$, the combined length $L_2$ of side wall portion 62 and guide flap 64 is greater than first length $L_1$, and the combined length $L_3$ of side wall portion 66 and guide flap 68 is greater than second length $L_2$. In addition, guide flap 64 has a width $W_1$ approximately equal to the width $W_1$ of respective side wall portion 62, and guide flap 68 has a width $W_4$ that is greater than width $W_1$ of respective side wall portion 66. Guide flap 68 also has an opening 70 defined therein.

First blank 10 may also include a layer 72 of protective material on interior side 14 of first blank 10. The protective material may be formed from any material that enables the sleeve container to function as described herein. Example protective materials include, but are not limited to, metallic foil and the like. The protective material aids in shielding the injectable medicine from exposure to light, and also provides a particulate-free contact surface in which to engage an injection medical device.

Figure 2:
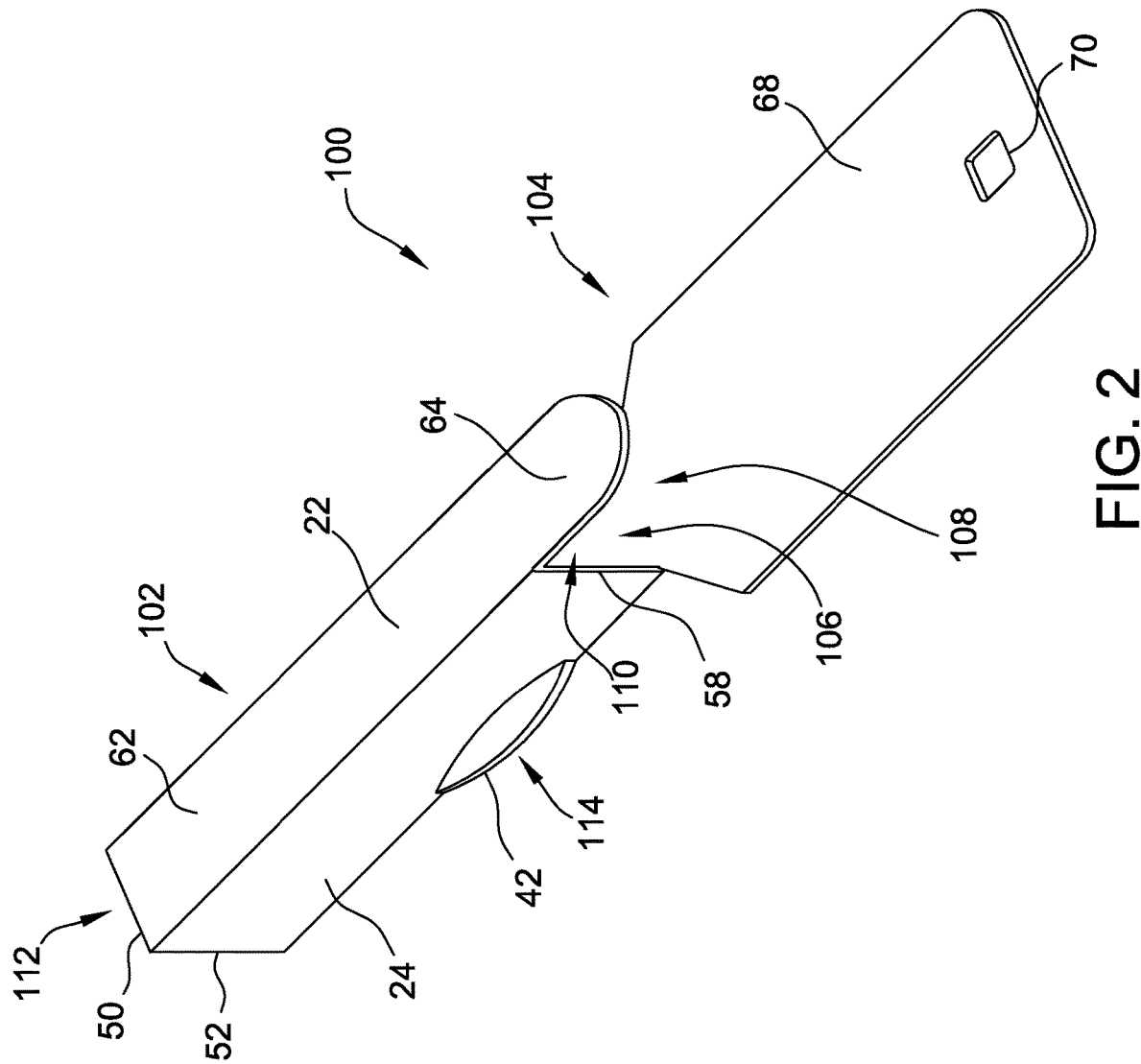
FIG. 2 is a first perspective view of the example sleeve container formed from the blank shown in FIG. 1.
Figure 3:
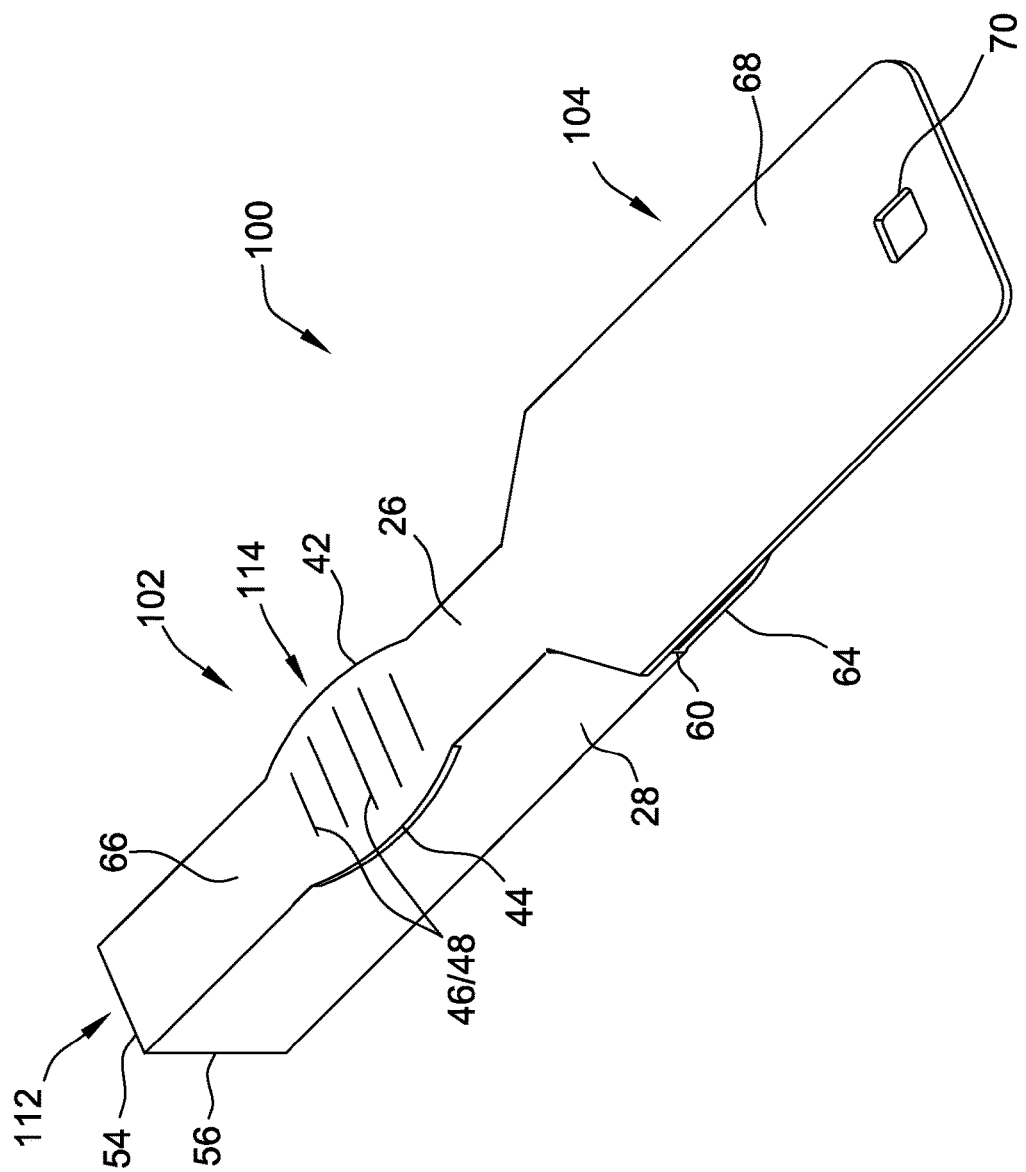
FIG. 3 is a second perspective view of the sleeve container shown in FIG. 2.

FIGS. 2 and 3 are perspective views of the example sleeve container 100 formed from first blank 10 (shown in FIG. 1). In the example embodiment, sleeve container 100 includes a sleeve portion 102 and an insertion portion 104. Sleeve portion 102 is formed from side panels 24 and 28, and from side wall portions 62 and 66, to define an interior cavity 106. Insertion portion 104 is formed from guide flaps 64 and 68, which are positioned on opposing sides of sleeve container 100 to define an insertion guide channel 108 that is in communication with interior cavity 106. More specifically, sleeve portion 102 includes a first open end 110 defined between top edges 58 and 60, first open end 110 providing access to interior cavity 106 from insertion guide channel 108. Sleeve portion 102 also includes a second open end 112, defined by bottom edges 50, 52, 54, and 56, that provides access to interior cavity 106.

Sleeve portion 102 also includes a gripping region 114, defined by cut lines 38 and 40 (shown in FIG. 1), and formed from flaps 42 and 44. Gripping region 114 provides a consumer with a leverage point for moving sleeve container 100, such as for removal from an outer container.

Figure 4:
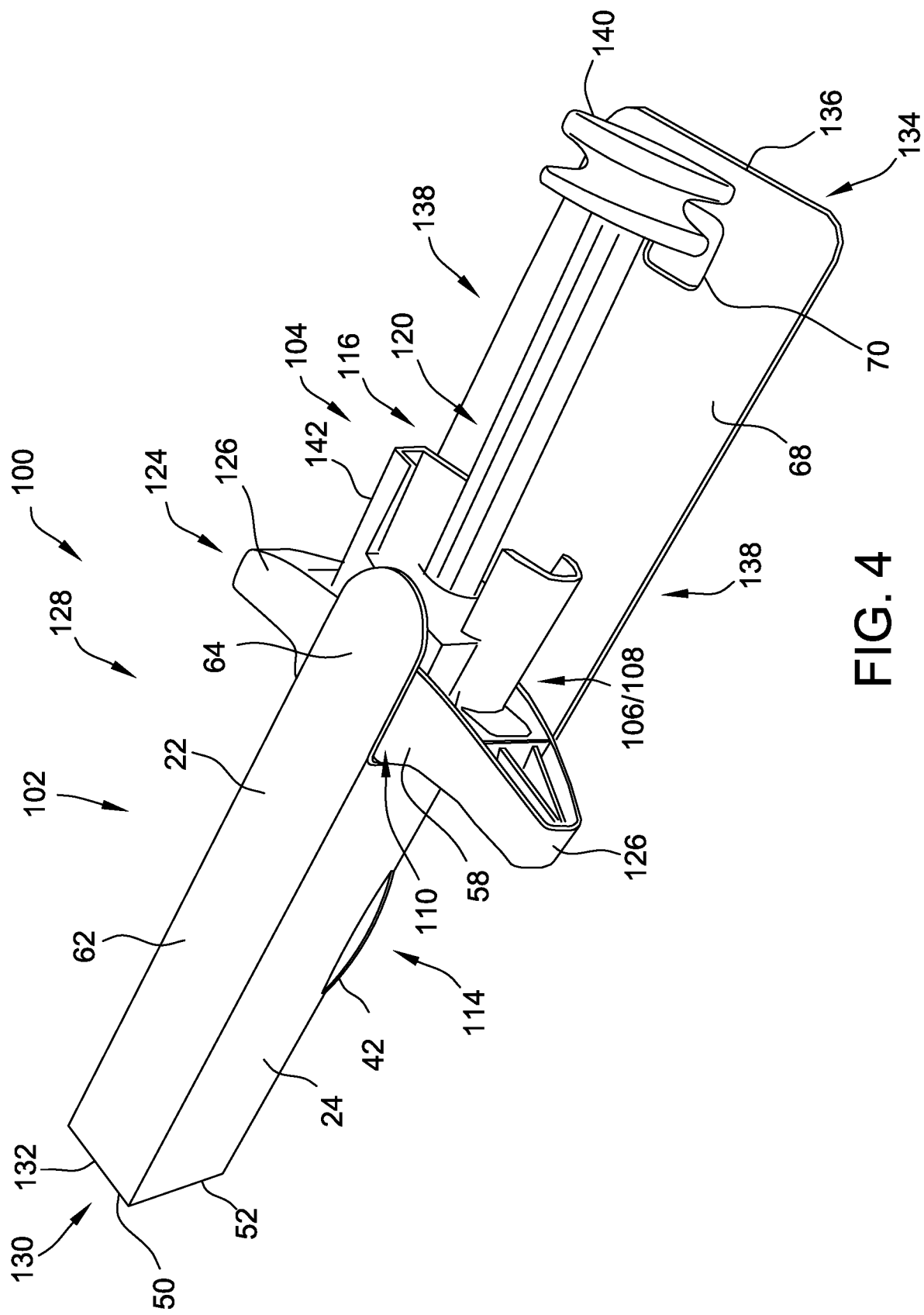
FIG. 4 is a perspective view of the sleeve container shown in FIG. 2 engaged with an example injection medical device.
Figure 5:
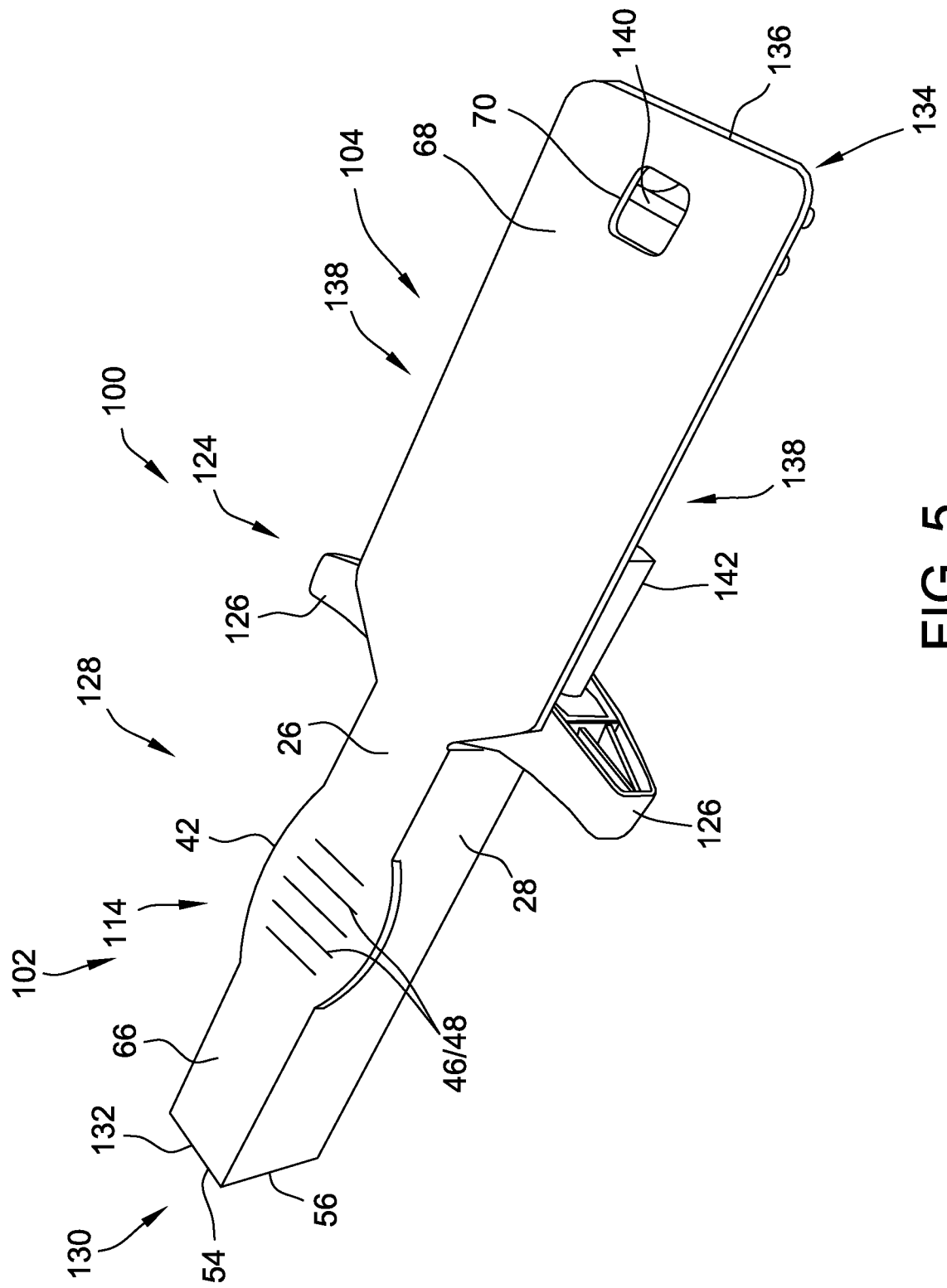
FIG. 5 is a perspective view of the sleeve container shown in FIG. 3 engaged with an example injection medical device.
Figure 14:
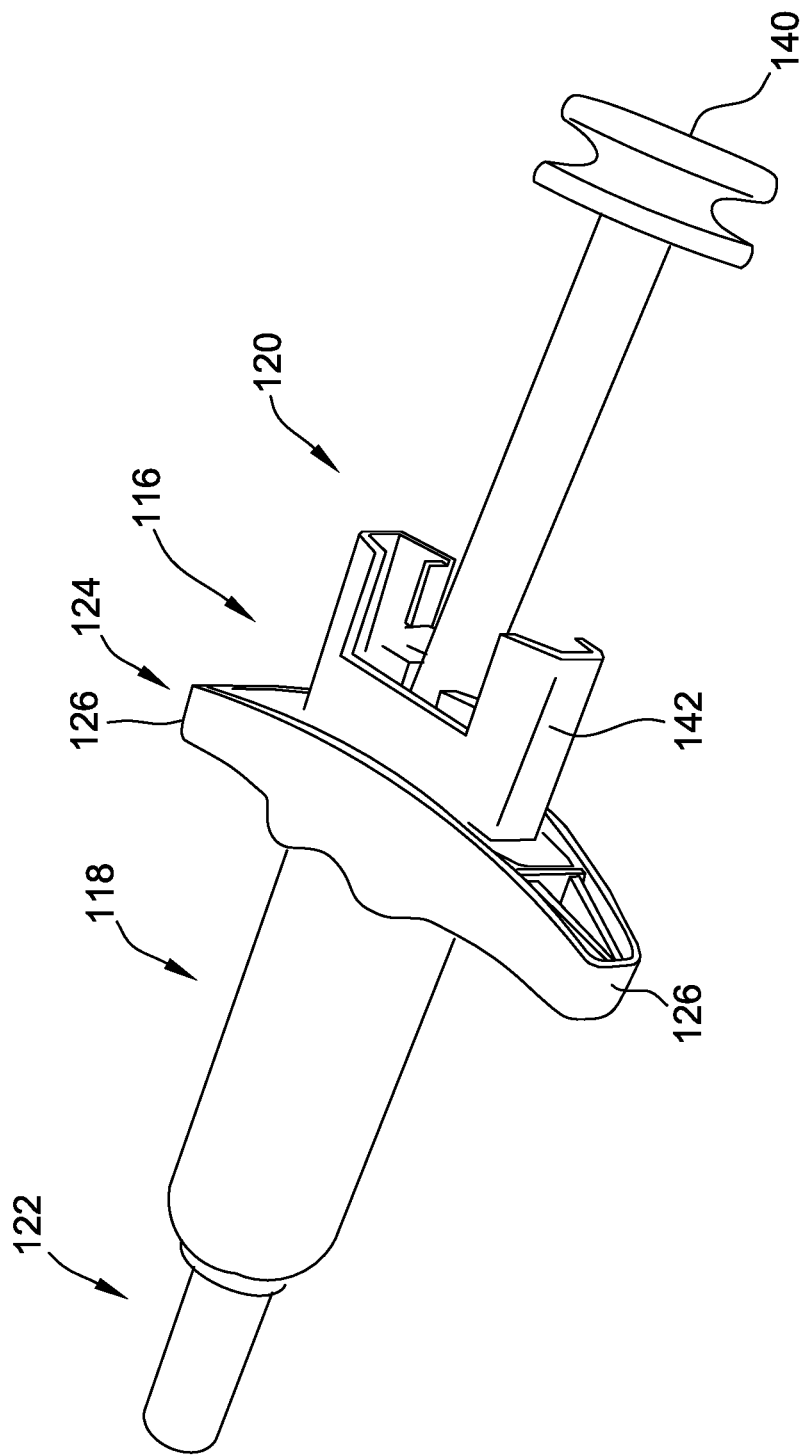
FIG. 14 is a perspective view of an example injection medical device that may be housed within the sleeve containers.

FIGS. 4 and 5 are perspective views of sleeve container 100 engaged with an example injection medical device 116. Referring to FIG. 14, injection medical device 116 includes a barrel portion 118, a plunger portion 120 translatable relative to the barrel portion 118, and a needle point 122 in communication with the barrel portion 118. Injection medical device 116 also includes a finger grip 124 coupled to barrel portion 118. Finger grip 124 includes a pair of projections 126 extending from barrel portion 118.

As shown in FIGS. 4 and 5, injection medical device 116 is engaged with sleeve container 100 to define a medication delivery system 128. To engage injection medical device 116 with sleeve container 100, injection medical device 116 is inserted, barrel-first, through insertion guide channel 108 and then into interior cavity 106. When fully inserted within sleeve container 100, barrel portion 118 is positioned within interior cavity 106, and plunger portion 120 protrudes from interior cavity 106. Sleeve portion 102 is configured to engage barrel portion 118 with an interference fit, which may be formed as a function of the size dimensions of panels 22, 24, 26, and 28, and of raised surface features 48. At insertion portion 104, guide flaps 64 and 68 are spaced from each other by a distance that enables finger grip 124 to be positioned therebetween. When injection medical device 116 is fully inserted within sleeve container 100, projections 126 abut top edges 58 and 60 to restrict further movement of injection medical device 116 relative to sleeve container 100 in the insertion direction.

Side panels 22, 24, 26, and 28, and guide flaps 64 and 64, are sized to provide buffer zones formed from the sheet material for protecting injection medical device 116 during storage and transportation. Buffer zones provide sleeve container 100 with additional sheet material for absorbing shock and vibrational forces, thereby reducing the impact of the shock and vibrational forces on injection medical device 116. For example, a first buffer zone 130 is defined at a leading edge 132 of sleeve portion 102, a second buffer zone 134 is defined at a trailing edge 136 of insertion portion 104, and a third buffer zone 138 is defined on lateral sides of insertion portion 104. First buffer zone 130 facilitates protecting needle point 122 (shown in FIG. 14), second buffer zone 134 facilitates protecting a plunger head 140 of plunger portion 120, and third buffer zone 138 facilitates protecting a base 142 of plunger portion 120. As will be described in more detail below, buffer zones 130, 134, and 138 also facilitate engagement with an outer container to facilitate restricting movement of medication delivery system 128 therein.

Figure 6:
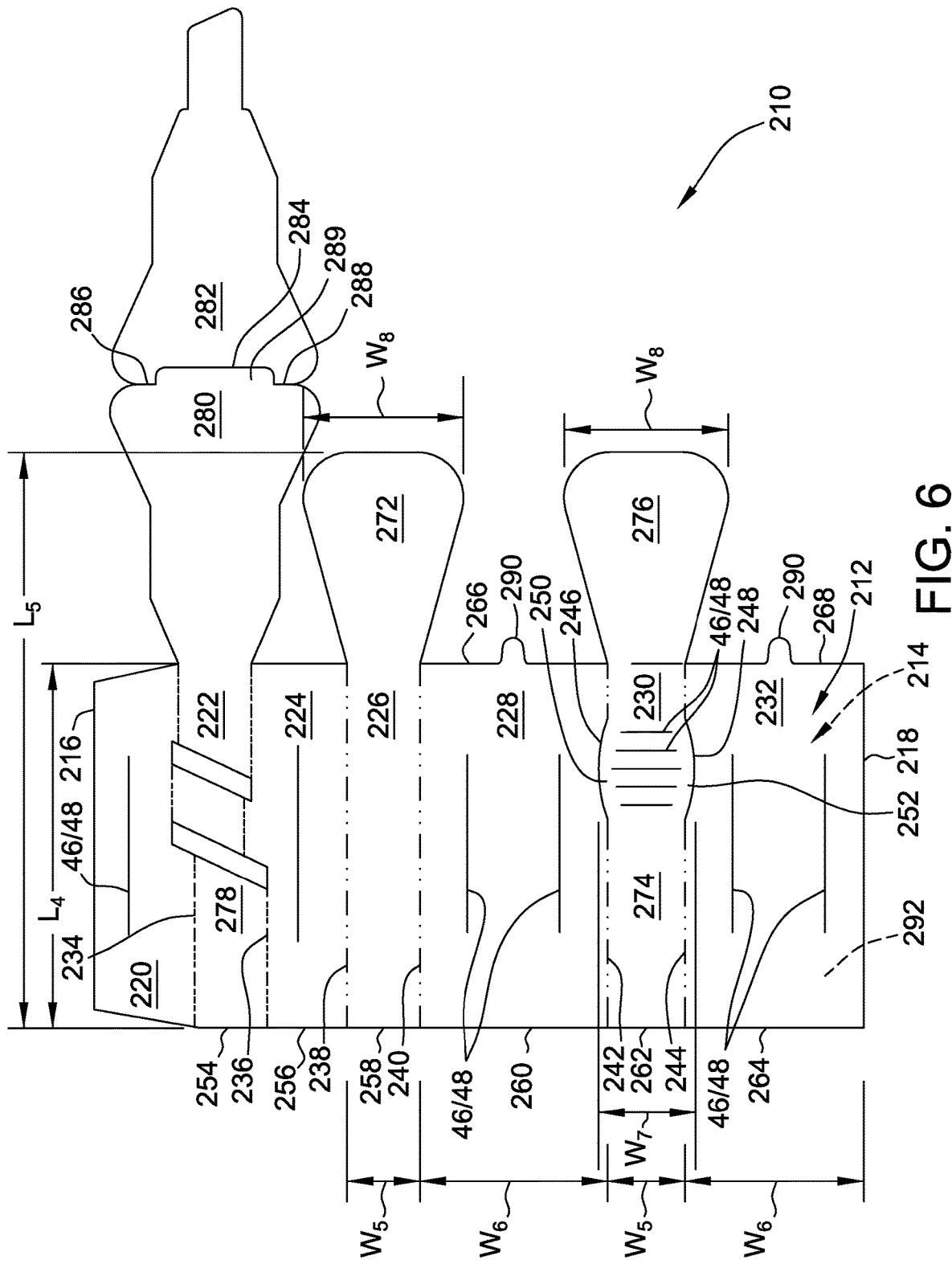
FIG. 6 illustrates a blank of sheet material for forming an additional sleeve container.

FIG. 6 illustrates a second blank 210 of sheet material for forming a sleeve container in accordance with another embodiment of the disclosure. In the example embodiment, second blank 210 has a first or exterior surface 212, and an opposing second or interior surface 214. Further, first blank 210 defines a leading edge 216 and an opposing trailing edge 218. Moreover, first blank 210 includes, from leading edge 216 to trailing edge 218, a joining tab 220, a divider panel 222, a joining panel 224, a first elongated side panel 226, a first side panel 228, a second elongated side panel 230, and a second side panel 232 coupled together along preformed, generally parallel fold lines 234, 236, 238, 240, 242, and 244, respectively.

Side panels 226 and 230 have a width $W_5$, and side panels 228 and 232 have a width $W_6$ that is greater than width $W_5$. Fold lines 234 and 236 are oriented in different direction across second blank 210, such that panels 222 and 224 have varying widths. It should be understood that the plurality of side panels, the divider panel, and the joining panel can each have any suitable size, shape, and/or configuration that enables blank 210 and/or the sleeve container to function as described herein. Additionally, although joining tab 220, divider panel 222, joining panel 224, first elongated side panel 226, first side panel 228, second elongated side panel 230, and second side panel 232 are specifically referred to herein, it should be noted that joining tab 220, divider panel 222, joining panel 224, first elongated side panel 226, first side panel 228, second elongated side panel 230, and second side panel 232 can collectively be referred to as side panels or side walls, divider panels or divider walls, or joining panels or joining walls.

Divider panel 222 extends from joining tab 220 along fold line 234, joining panel 224 extends from divider panel 222 along fold line 236, elongated side panel 226 extends from joining panel 224 along fold line 238, side panel 228 extends from side panel 226 along fold line 240, side panel 230 extends from side panel 228 along fold line 242, and side panel 232 extends from side panel 230 along fold line 244. In addition, a first cut line 246 is defined along a portion of fold line 242, and a second cut line 248 is defined along a portion of fold line 244. First cut line 246 defines a first gripping flap 250 on side panel 230, and second cut line 248 defines a second gripping flap 252 on side panel 230. Cut lines 246 and 248 have an arcuate shape and are convex relative to a centerline of side panel 230. Accordingly, the portion of side panel 230 defined between cut lines 246 and 248 has a width $W_7$ greater than width $W_5$ of side panel 230 itself. Alternatively, gripping flaps 250 and 252 may have any shape that enables the sleeve container to function as described herein. Panels 220, 224, 228, 230, and 232 also include debossing lines 46 on first side 212 thereof. Debossing lines 46 facilitate creating raised surface features 48 on second side 214 of panels 220, 224, 228, 230, and 232. Raised surface features 48 facilitate engagement between the sleeve container and a product positioned therein.

Panels 222, 224, 226, 228, 230, and 232 each include bottom edges 254, 256, 258, 260, 262, and 264, respectively, and which are all aligned with each other. Panels 228 and 232 also include top edges 266 and 268, respectively, which are aligned with each other. Side panel 226 includes a side wall portion 270 and a guide flap 272, and side panel 230 includes a side wall portion 274 and a guide flap 276. Guide flaps 272 and 276 extend beyond top edges 266 and 268. Accordingly, side panels 228 and 232, and side wall portions 270 and 274, have a length $L_4$, and the length $L_5$ of panels 226 and 230 is greater than length $L_4$. In addition, guide flaps 272 and 276 have a width $W_8$ that is greater than width $W_5$ of respective side panels 226 and 230.

Divider panel 222 includes a divider portion 278 and a guide flap 280 extending beyond top edges 266 and 268. Divider panel 222 also includes a reinforcement panel 282 extending from guide flap 280. Reinforcement panel 282 is defined by a cut line 284, and extends from guide flap 280 along fold lines 286 and 288. Cut line 284 also defines a retaining flap 289 on guide flap 280. In addition, panels 228 and 232 each include a projection 290 extending from top edges 266 and 268, respectively. Second blank 210 may also include a layer 292 of protective material on interior side 214 of second blank 210.

Figure 7:
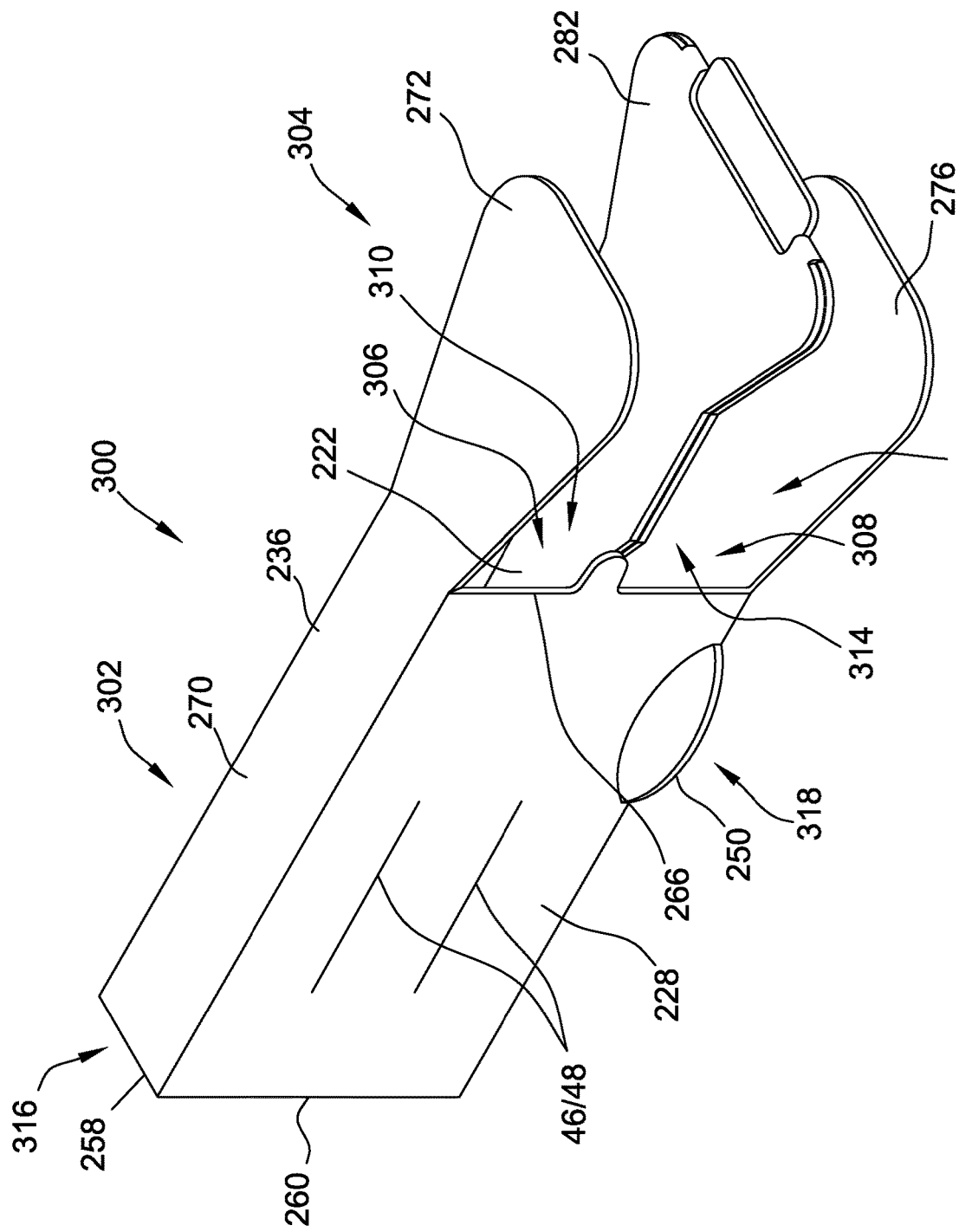
FIG. 7 is a first perspective view of the additional sleeve container formed from the blank shown in FIG. 6.
Figure 8:
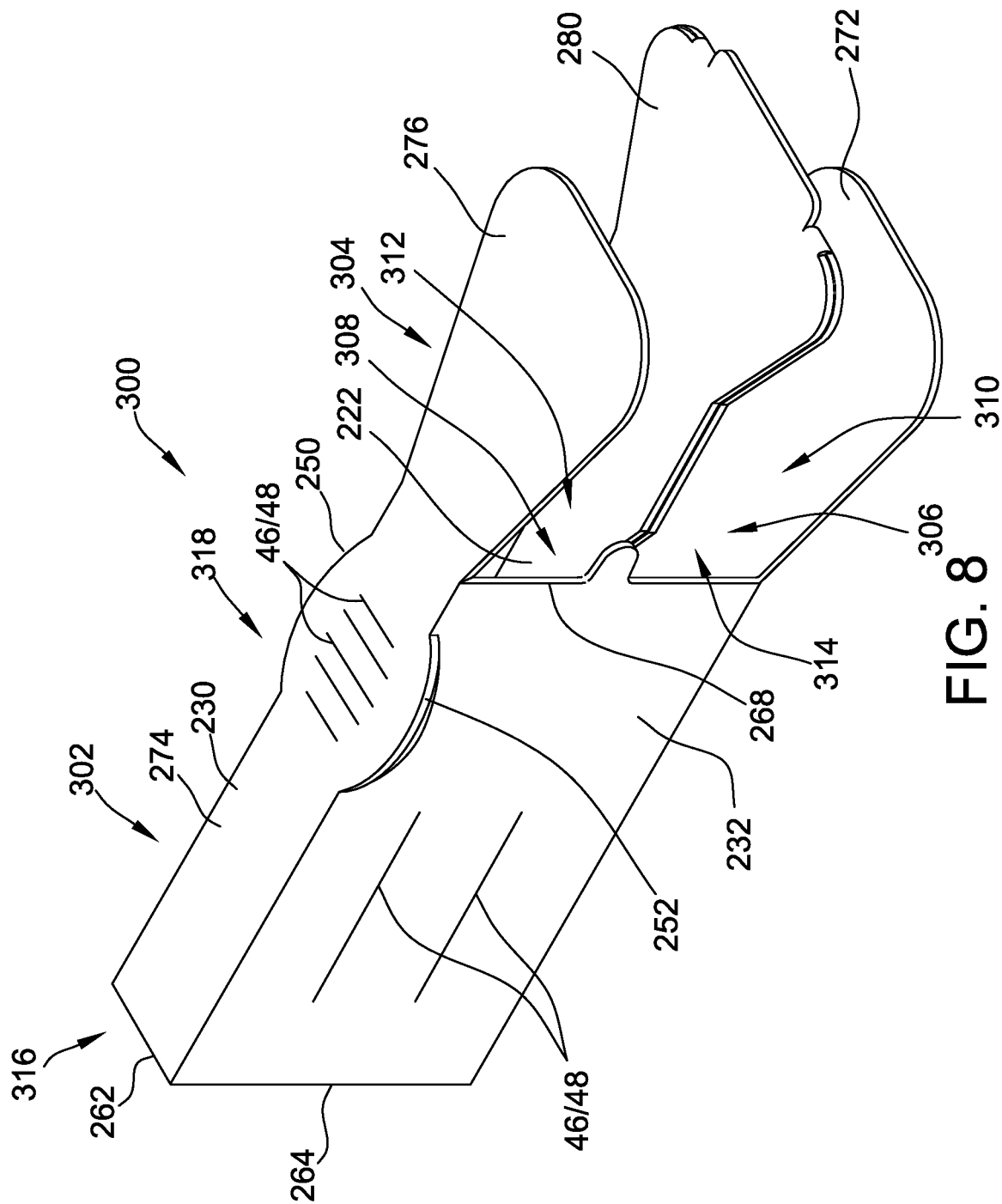
FIG. 8 is a second perspective view of the sleeve container shown in FIG. 7

FIGS. 7 and 8 are perspective views of the additional sleeve container 300 formed from second blank 210 (shown in FIG. 6). In the example embodiment, sleeve container 300 includes a sleeve portion 302 and an insertion portion 304. Sleeve portion 302 is formed from panels 222, 224 (shown in FIG. 6), 228, and 232, and from side wall portions 270 and 274, to define a first interior cavity 306 and a second interior cavity 308 defined as a result of partitioning of sleeve portion 302 by divider portion 278 (shown in FIG. 6) of divider panel 222. Insertion portion 304 is formed from flaps 272 and 276, and from flap 280 and panel 282, to define a first insertion guide channel 310 between flap 272 and combined flap/panel 280 and 282, and a second insertion guide channel 312 between flap 276 and combined flap/panel 280 and 282. First insertion guide channel 310 is in communication with first interior cavity 306, and second insertion guide channel 312 is in communication with second interior cavity 308. More specifically, sleeve portion 302 includes a first open end 314 defined between top edges 266 and 268, first open end 314 providing access to interior cavities 306 and 308 from respective insertion guide channels 310 and 312. Sleeve portion 302 also includes a second open end 316, defined by bottom edges 254, 256, 258, 260, 262, and 264, that provides access to interior cavities 306 and 308.

Sleeve portion 302 also includes a gripping region 318, defined by cut lines 246 and 248 (shown in FIG. 6), and formed from flaps 250 and 252. Gripping region 318 provides a consumer with a leverage point for moving sleeve container 300, such as for removal from an outer container.

Figure 9:
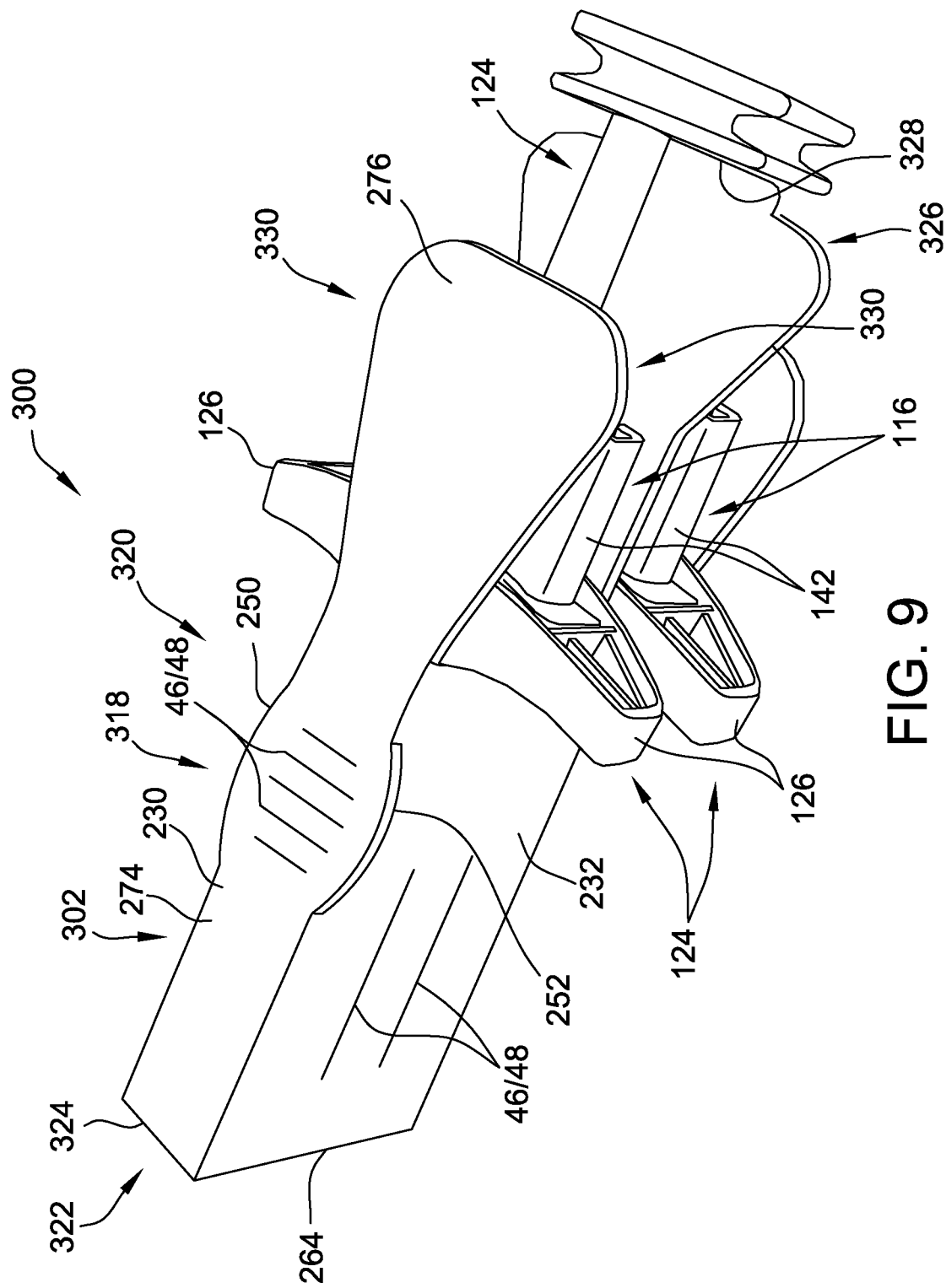
FIG. 9 a perspective view of the sleeve container shown in FIG. 8 engaged with example injection medical devices.

FIG. 9 is a perspective view of sleeve container 300 engaged with example injection medical devices 116 to define a medication delivery system 320. To engage injection medical devices 116 with sleeve container 300, injection medical devices 116 are inserted, barrel-first, through insertion guide channels 310 and 312 and then into respective interior cavities 306 and 308. When fully inserted within sleeve container 300, each barrel portion 118 (shown in FIG. 14) is positioned within interior cavities 306 and 308, and each plunger portion 120 protrudes from interior cavities 306 and 308. Sleeve portion 302 is configured to engage each barrel portion 118 with an interference fit, which may be formed as a function of the size dimensions of panels 226, 228, 230, and 232, of the partitioning of sleeve portion 302 by panel 222, and of raised surface features 48. At insertion portion 304, guide flaps 272 and 276 are spaced from combined flap/panel 280 and 282 by a distance that enables finger grip 124 to be positioned therebetween within respective insertion guide channels 310 and 312. When injection medical devices 116 are fully inserted within sleeve container 300, projections 126 abut top edges 266 and 268 to restrict further movement of injection medical devices 116 relative to sleeve container 300 in the insertion direction.

Panels 222, 224, 226, 228, 230, and 232, and guide flaps 272, 276, and 280, and reinforcement panel 282, are sized to provide buffer zones formed from the sheet material for protecting injection medical devices 116 during storage and transportation. Buffer zones provide sleeve container 300 with additional sheet material for absorbing shock and vibrational forces, thereby reducing the impact of the shock and vibrational forces on injection medical devices 116. For example, a first buffer zone 322 is defined at a leading edge 324 of sleeve portion 302, a second buffer zone 326 is defined at a trailing edge 328 of insertion portion 304, and a third buffer zone 330 is defined on lateral sides of insertion portion 304. First buffer zone 322 facilitates protecting needle point 122 (shown in FIG. 14), second buffer zone 326 is designed to directly engage an outer container, as will be described in more detail below, and third buffer zone 330 facilitates protecting base 142 of plunger portion 120. As will be described in more detail below, buffer zones 322, 326, and 330 also facilitate engagement with an outer container to facilitate restricting movement of medication delivery system 320 therein.

Figure 10:
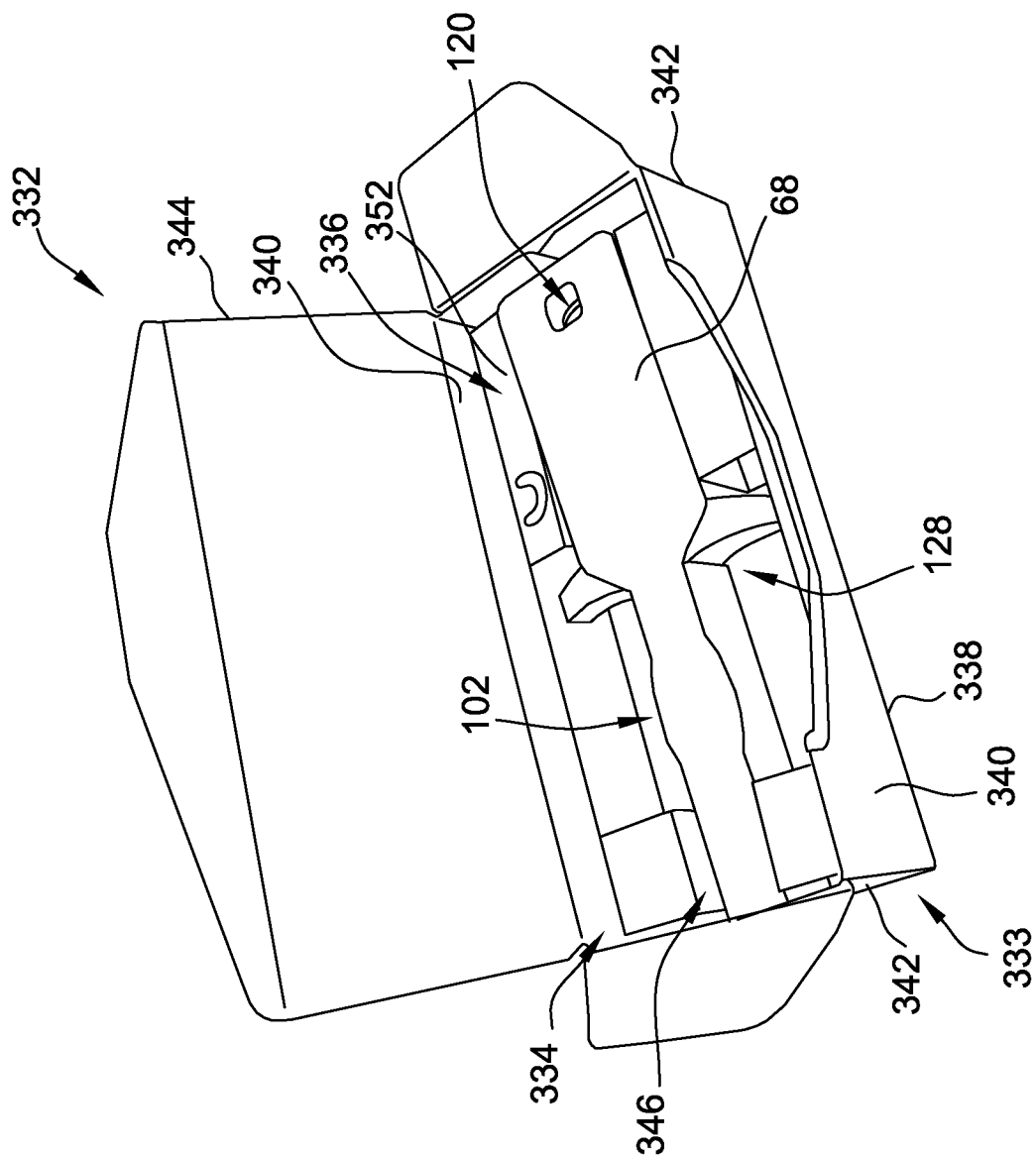
FIG. 10 is a perspective view of an example container assembly for use with the sleeve container shown in FIGS. 4 and 5, the container assembly including an outer container in an open position with an example medication delivery system positioned therein.
Figure 11:
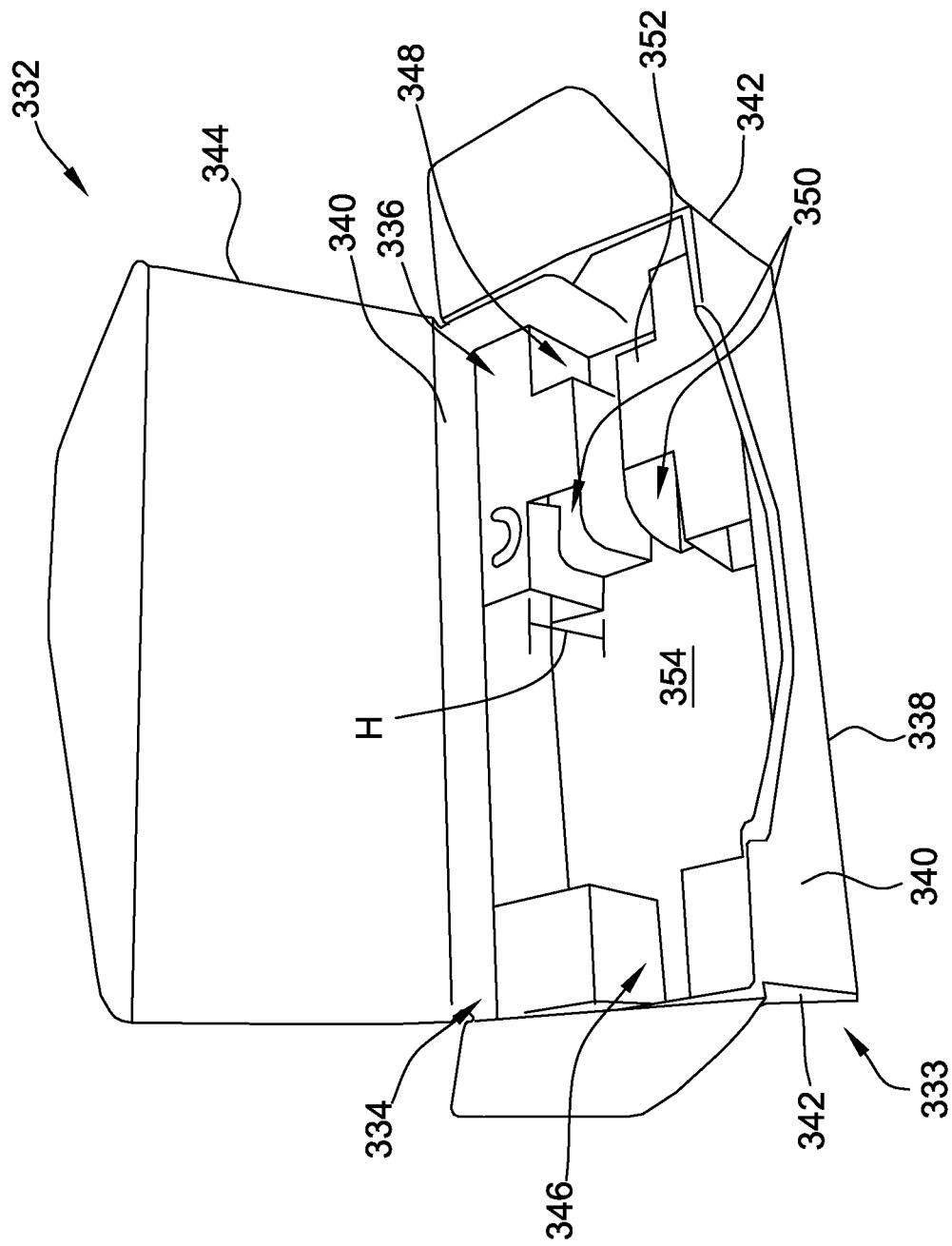
FIG. 11 is a perspective view of the container assembly shown in FIG. 10 without the medication delivery system positioned therein.

FIGS. 10 and 11 are perspective views of an example outer container 332 in an open position with and without medication delivery system 128 positioned therein. In the example embodiment, outer container 332 includes a container portion 333 including an interior 334, and a holder insert 336 positioned within interior 334. Interior 334 of container portion 333 is defined from a bottom wall 338, a pair of side walls 340, a pair of end walls 342, and a closure flap 344 selectively rotatable to open and close outer container 332.

Holder insert 336 is formed from a blank of sheet material includes, folded to define numerous features that engage medication delivery system 128 to facilitate protecting injection medical device 116 during storage and transport. For example, holder insert 336 includes a first slot 346 for receiving sleeve portion 102 of sleeve container 100, a second slot 348 for receiving plunger portion 120 of injection medical device 116, and a third slot 350 for receiving base 142 of plunger portion 120. Holder insert 336 also includes a top surface 352 oriented perpendicularly relative to side walls 340 and end walls 342.

When medication delivery system 128 engaged with holder insert 336, sleeve portion 102 is positioned within first slot 346, plunger portion 120 is positioned within second slot 348, and base 142 is positioned within third slot 350. Accordingly, at least first buffer zone 130 and second buffer zone 134 (both shown in FIGS. 4 and 5) on sleeve container 100 are positioned to absorb shock and vibrational forces induced from end walls 342. In one embodiment, third slot 350 is sized to receive base 142 with a minimal clearance fit to facilitate restricting lateral movement of medication delivery system 128 within outer container 332. In addition, guide flap 68 is engaged with top surface 352, which is spaced by a height H from a base 354 of holder insert 336. Height H is selected such that medication delivery system 128 is at least partially suspended within outer container 332 when guide flap 68 is engaged with top surface 352. As such, shock and vibrational forces are absorbed by guide flap 68.

Figure 12:
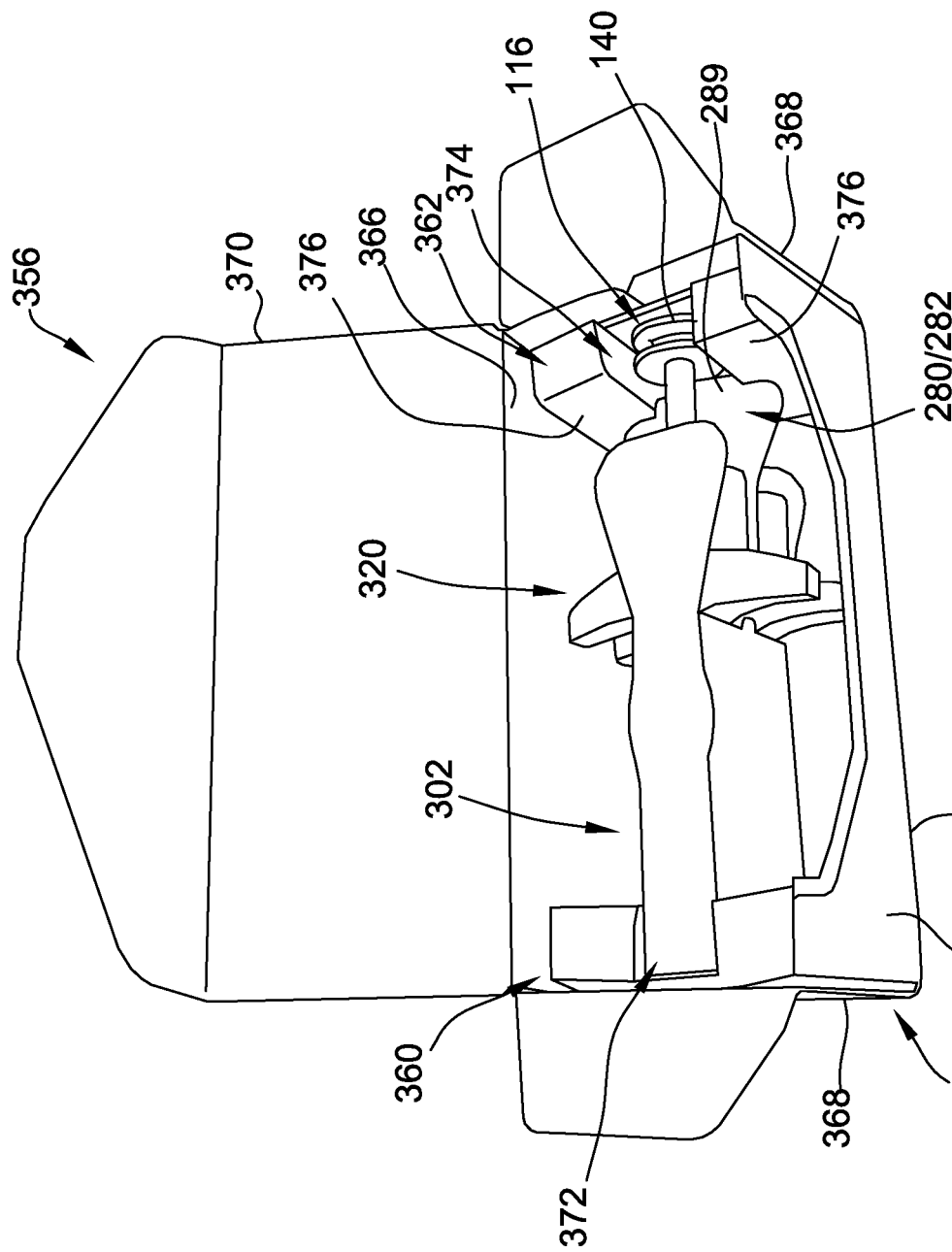
FIG. 12 is a perspective view of an example container assembly for use with the sleeve container shown in FIG. 9, the container assembly including an outer container in an open position with an additional medication delivery system positioned therein.
Figure 13:
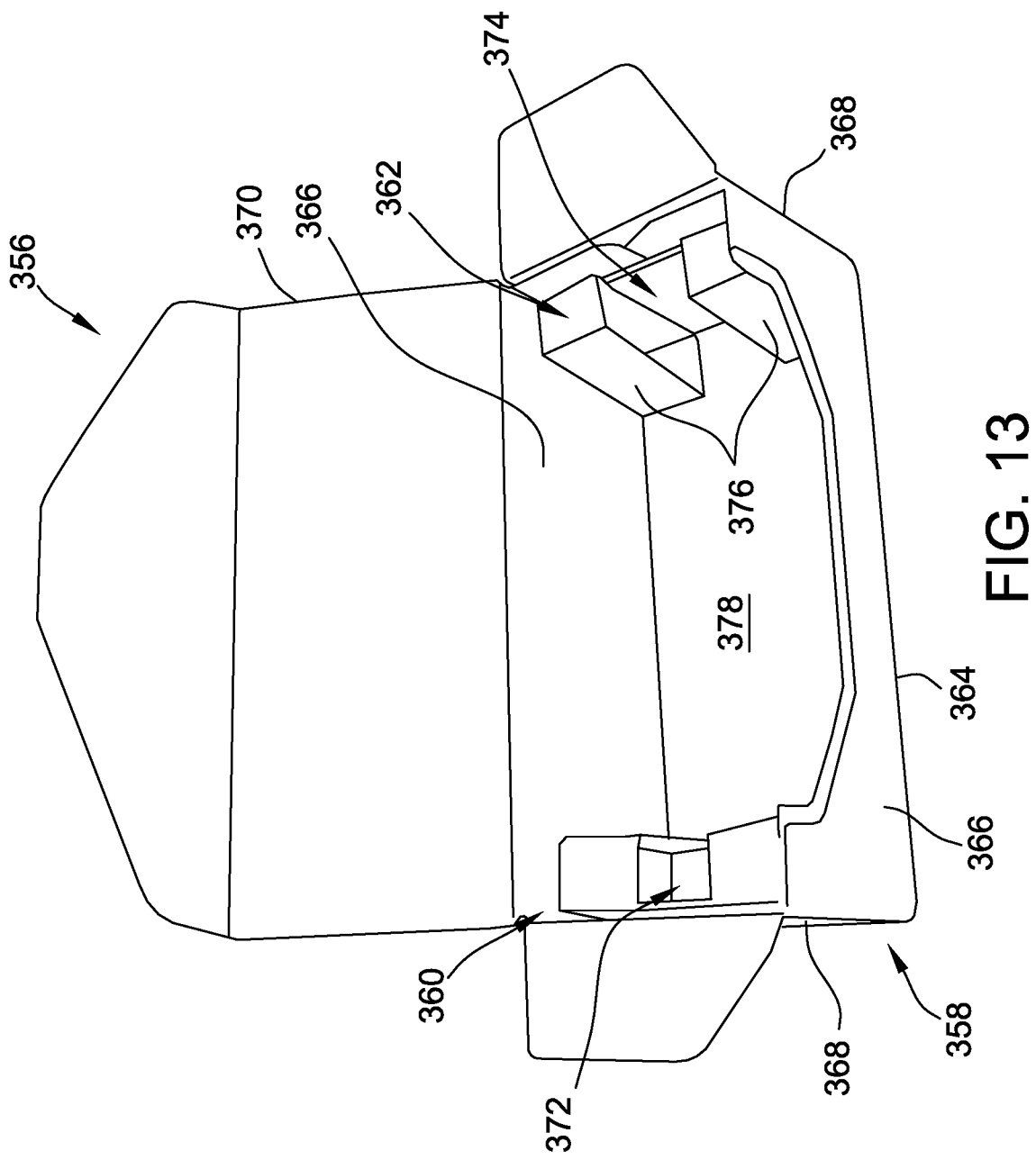
FIG. 13 is a perspective view of the container assembly shown in FIG. 12 without the medication delivery system positioned therein.

FIGS. 12 and 13 are perspective views of an additional outer container 356 in an open position with and without medication delivery system 320 positioned therein. In the example embodiment, outer container 356 includes a container portion 358 including an interior 360, and a holder insert 362 positioned within interior 360. Interior 360 of container portion 358 is defined from a bottom wall 364, a pair of side walls 366, a pair of end walls 368, and a closure flap 370 selectively rotatable to open and close outer container 356.

Holder insert 362 is formed from a blank of sheet material includes, folded to define numerous features that engage medication delivery system 320 to facilitate protecting injection medical device 116 during storage and transport. For example, holder insert 362 includes a first slot 372 for receiving sleeve portion 302 of sleeve container 300, and a second slot 374 for receiving plunger head 140 of plunger portion 120. Holder insert 362 also includes a pair of vertical walls 376 oriented perpendicularly to a base 378 of holder insert 362.

When medication delivery system 320 engaged with holder insert 362, sleeve portion 302 is positioned within first slot 372, and plunger head 140 of plunger portion 120 is positioned within second slot 374. Accordingly, at least first buffer zone 322 and second buffer zone 326 (both shown in FIG. 11) on sleeve container 300 are positioned to absorb shock and vibrational forces induced from end walls 368. For example, second buffer zone 326 absorbs forces induced from end walls 368 and transferred to medication delivery system 320 via holder insert 362. Accordingly, guide flap 280 and panel 282 abut against vertical walls 376 to absorb the shock and vibrational forces. In addition, retaining flap 289 is received within second slot 374 to facilitate restricting lateral movement of medication delivery system 320 within outer container 356.

Figure 15:
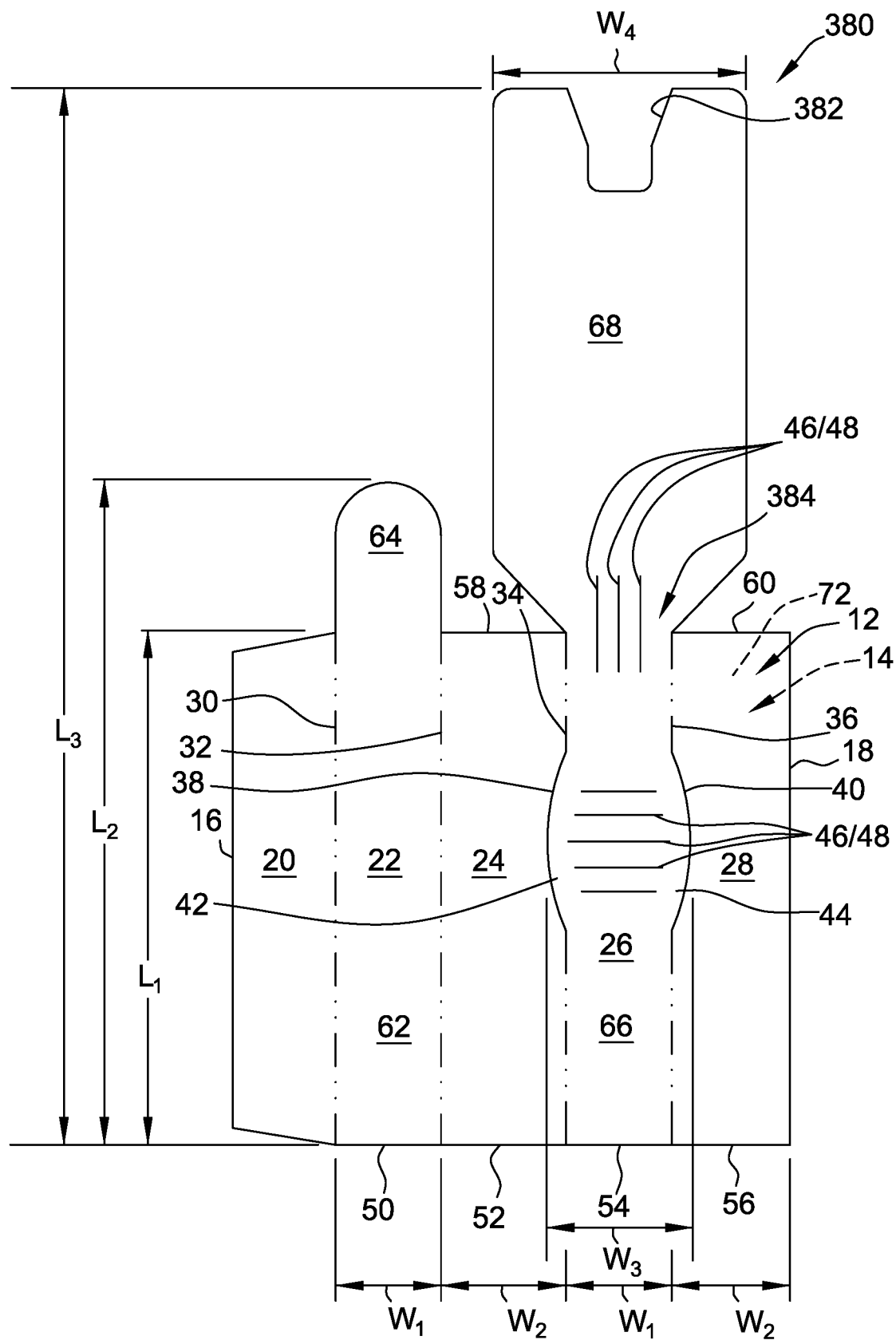
FIG. 15 illustrates a blank of sheet material for forming an additional sleeve container.

FIG. 15 illustrates a third blank 380 of sheet material for forming an additional sleeve container. In the example embodiment, third blank 380 includes guide flap 68, and guide flap 68 has a notch 382 defined therein. In addition side panel 26 includes a neck portion 384 defined between side wall portion 66 and guide flap 68. Neck portion 384 defines an area on side panel 26 that transitions between width $W_1$ and width $W_4$. Neck portion 384 includes debossing lines 46 on first side 12 thereof. Debossing lines 46 facilitate strengthening neck portion 384 and limiting deformation and bending of guide flap 68 relative to side wall portion 66.

Figure 16:
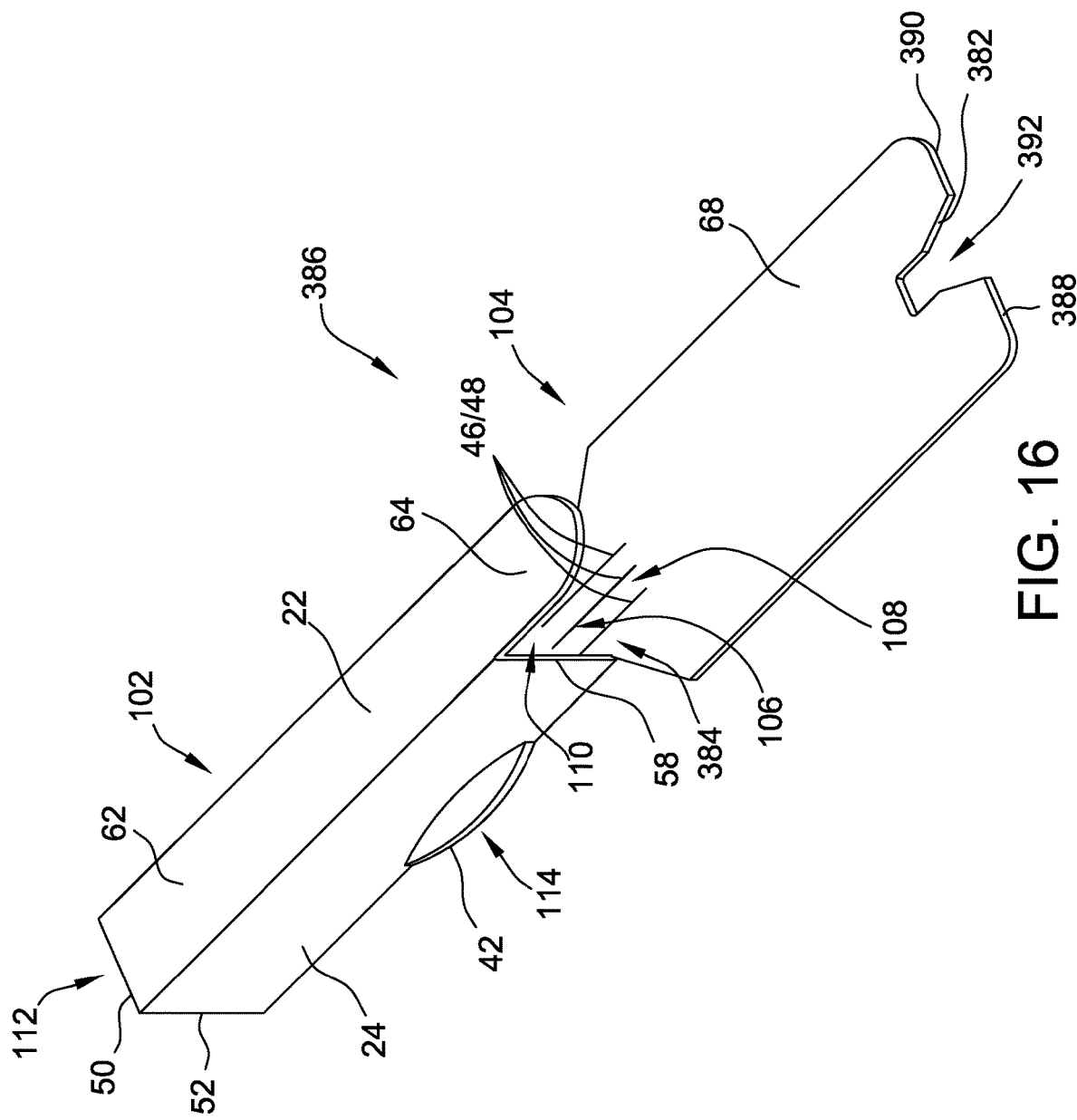
FIG. 16 is a first perspective view of the additional sleeve container formed from the blank shown in FIG. 15.
Figure 17:
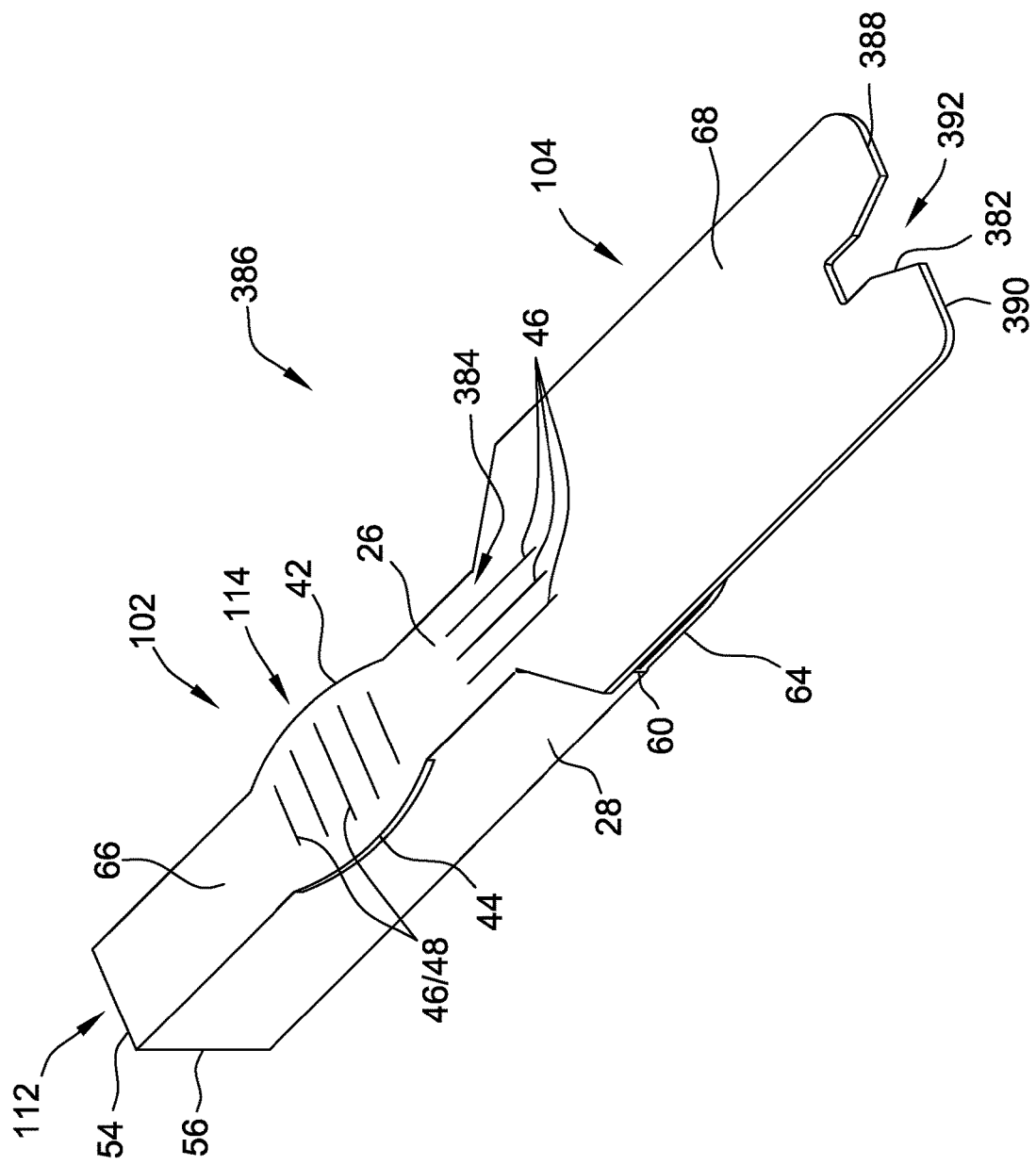
FIG. 17 is a second perspective view of the sleeve container shown in FIG. 16.

FIGS. 16 and 17 are perspective views of the additional sleeve container 386 formed from third blank 380 (shown in FIG. 15). In the example embodiment, notch 382 on guide flap 68 defines a first top edge 388 and a second top edge 390 on guide flap 68 such that a gap 392 is defined between first top edge 388 and second top edge 390. As described above, injection medical device 116 (shown in FIG. 14) is inserted, barrel-first, through insertion guide channel 108 and then into interior cavity 106. As injection medical device 116 is inserted into interior cavity 106, plunger head 140 of plunger portion 120 (both shown in FIG. 14) is moved from beyond top edges 388 and 390 into a seated position in which plunger head 140 is covered by guide flap 68. Gap 392 facilitates movement of plunger head 140 into the seated position without potentially being obstructed by material of sleeve container 386.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A blank of sheet material for forming a sleeve container, the blank of sheet material comprising:
    two side panels each comprising a bottom edge and a top edge; and
    two elongated side panels arranged alternatingly with the side panels, wherein a plurality of fold lines are defined between the side panels and the elongated side panels, wherein the elongated side panels each respectively comprise a side panel portion and a guide flap extending beyond the top edge of the side panels, wherein the side panels and the side panel portions of the elongated side panels are configured to define an interior cavity of the sleeve container, and wherein the guide flaps are configured to define an insertion guide channel that is in communication with the interior cavity,
    wherein a pair of cut lines are defined along a portion of adjacent fold lines of the plurality of fold lines on either side of one of the elongated side panels, wherein the pair of cut lines are symmetrical across the elongated side panel between the cut lines and are configured to define a gripping region on the elongated side panel defined between the cut lines, and wherein the cut lines are oriented such that the gripping region has a greater width than the elongated side panel from which the gripping region extends.

2. The blank of sheet material in accordance with claim 1 a joining tab extending from one of the side panels or one of the elongated side panels.

3. The blank of sheet material in accordance with claim 1 further comprising a joining panel extending from one of the side panels or one of the elongated side panels, a divider panel extending from the joining panel, and a joining tab extending from the divider panel.

4. The blank of sheet material in accordance with claim 3, wherein the divider panel comprises a divider portion configured to partition the interior cavity of the sleeve container, and a guide flap extending beyond the top edge of the side panels.

5. The blank of sheet material in accordance with claim 4 further comprising a reinforcement panel extending from the guide flap of the divider panel, wherein a fold line is defined between the guide flap of the divider panel and the reinforcement panel.

6. The blank of sheet material in accordance with claim 1, wherein the guide flap of at least one of the elongated side panels has a greater width than the side panel portion associated therewith.

7. The blank of sheet material in accordance with claim 1 further comprising an opening defined in the guide flap of at least one of the elongated side panels.

8. A sleeve container comprising:
    two side walls each comprising a bottom edge and a top edge; and
    two elongated side walls arranged alternatingly with and perpendicular to the side walls, wherein a plurality of fold lines are defined between the side walls and the elongated side walls, wherein the elongated side walls each respectively comprise a side wall portion and a guide flap extending beyond the top edge of the side walls, wherein the side walls and the side wall portions of the elongated side walls define a sleeve portion of the sleeve container, the sleeve portion comprising an interior cavity, and wherein the guide flaps are configured to define an insertion guide channel that is in communication with the interior cavity,
    wherein a pair of cut lines are defined along a portion of adjacent fold lines of the plurality of fold lines on either side of one of the elongated side walls, wherein the pair of cut lines are symmetrical across the elongated side wall between the cut lines and are configured to define a gripping region on the elongated side wall defined between the cut lines, and wherein the pair of cut lines are oriented such that the gripping region has a greater width than the elongated side wall defined between the cut lines.

9. The sleeve container in accordance with claim 8, wherein the side walls and the elongated side walls are formed from a blank of sheet material, the sleeve container further comprising a layer of protective material on one side of the blank of sheet material.

10. The sleeve container in accordance with claim 8 further comprising at least one debossing line on at least one of the side walls or the elongated side walls, the at least one debossing line configured to define a raised surface feature within the at least one interior cavity.

11. The sleeve container in accordance with claim 8 further comprising a divider wall extending between the side walls for partitioning the interior cavity into a pair of interior cavities within the sleeve portion.

12. The sleeve container in accordance with claim 11, wherein the divider wall comprises a divider guide flap extending beyond the top edge of the side walls, the divider guide wall configured to partition the insertion guide channel into a pair of insertion guide channels.

13. The sleeve container in accordance with claim 8, wherein the sleeve portion comprises a pair of open ends that provide access to the interior cavity.

14. A medication delivery system in accordance with claim 8 comprising an injection medical device that comprises a barrel portion and a plunger portion, wherein the barrel portion is positionable within the interior cavity of the sleeve portion and the plunger portion protrudes from interior cavity.

15. The medication delivery system in accordance with claim 14, wherein the sleeve portion is sized to engage the barrel portion with an interference fit.

16. A container assembly formed from a plurality of blanks of sheet material, the container assembly comprising:
    a medication delivery system comprising a sleeve container configured to receive an injection medical device, the sleeve container comprising:
        two side walls each comprising a bottom edge and a top edge; and
        two elongated side walls arranged alternatingly with and perpendicular to the side walls, wherein a plurality of fold lines are defined between the side walls and the elongated side walls, wherein the elongated side walls each respectively comprise a side wall portion and a guide flap extending beyond the top edge of the side walls, wherein the side walls and the side wall portions of the elongated side walls define a sleeve portion of the sleeve container, the sleeve portion comprising an interior cavity, and wherein the guide flaps are configured to define an insertion guide channel that is in communication with the interior cavity, wherein a pair of cut lines are defined along a portion of adjacent fold lines of the plurality of fold lines on either side of one of the elongated side walls, wherein the pair of cut lines are symmetrical across the elongated side wall between the cut lines and are configured to define a gripping region on the elongated side wall defined between the cut lines, and wherein the pair of cut lines are oriented such that the gripping region has a greater width than the elongated side wall defined between the cut lines; and a carton comprising:

a container portion comprising an interior; and a holder insert positioned within the interior, wherein the holder insert comprises a first slot configured to receive the sleeve portion of the sleeve container, and a second slot configured to receive a portion of the injection medical device.

17. The container assembly in accordance with claim 16, wherein the holder insert comprises at least one interior side wall configured to engage at least one of the side walls or elongated side walls to restrict movement of the sleeve container relative to the holder insert.

\* \* \* \* \*